US00PP37034P2

(12) United States Plant Patent
Shigematsu et al.

(10) Patent No.: US PP37,034 P2
(45) Date of Patent: Oct. 21, 2025

(54) ***MANDARIN* PLANT NAMED 'Mikanken10'**

(50) Latin Name: ***Citrus* sp.**
Varietal Denomination: Mikanken10

(71) Applicant: EHIME PREFECTURE, Ehime (JP)

(72) Inventors: Yukinori Shigematsu, Ehime (JP); Takehiro Okusada, Ehime (JP); Keiji Kita, Ehime (JP); Hiromichi Yakushiji, Ehime (JP); Mitsutoshi Okamoto, Ehime (JP); Taizo Ninomiya, Ehime (JP); Yoji Hyodo, Ehime (JP); Takae Sakimoto, Ehime (JP); Haruhito Nakata, Ehime (JP); Saki Miyoshi, Ehime (JP); Saki Yamamoto, Ehime (JP); Toya Hioki, Ehime (JP); Yasuyuki Masamoto, Ehime (JP); Kei Kinoshita, Ehime (JP); Takehiro Kikuchi, Ehime (JP); Daijiro Sugawara, Ehime (JP); Hiroaki Mido, Ehime (JP)

(73) Assignee: EHIME PREFECTURE, Matsuyama (JP)

( * ) Notice: Subject to any disclaimer, the term of this patent is extended or adjusted under 35 U.S.C. 154(b) by 0 days.

(21) Appl. No.: 19/182,900

(22) Filed: Apr. 18, 2025

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./202, 201
CPC . A01H 5/08; A01H 5/00; A01H 6/785; A01H 6/78
See application file for complete search history.

(56) References Cited

PUBLICATIONS

Iwamasa, Citrus Cultivars in Japan, HortScience, vol. 23(4) 1988, 687-690. (Year: 1988).*
Ma et al. Effects of Postharvest Treatment with 1-Naphthaleneacetic Acid on Chlorophyll and Carotenoid Metabolism in Citrus Fruit, The Horticulture Journal 92 (4): 393-401, 2023. (Year: 2023).*

* cited by examiner

*Primary Examiner* — June Hwu
(74) *Attorney, Agent, or Firm* — Seckel IP, PLLC

(57) ABSTRACT

A new variety of *Citrus* sp. plant named 'Mikanken10' that has dense spines on the tree, leaf blade with emargination at tip, fruit with flattened general shape of distal part, and no navel opening.

4 Drawing Sheets

Common name: Mandarin.
Botanical classification: *Citrus* sp.
Variety denomination: 'Mikanken10'.

BACKGROUND OF THE NEW VARIETY

The present invention relates to a new and distinct variety of Mandarin, *Citrus* sp., which has been given the variety denomination 'Mikanken10'.

ORIGIN OF THE VARIETY

The parent varieties are 'ARIAKE' (male parent) (patented in the US as U.S. Plant Pat. No. 9,235) and 'NANKO' (female parent) (not patented in the U.S.), respectively.

The variety was developed and propagated in Uwajima, Ehime, Japan.

The variety was reproduced asexually by vegetative reproduction by top grafting one-year-old scions on rootstocks, in Uwajima, Ehime, Japan. The rootstock used was 'MIYAGAWAWASE' (not patented) as an interstock grafted onto *Poncirus trifoliata* (trifoliate orange).

In 1993, crossing the parent varieties and collecting seeds to be grown in the next year.

In 1994 and 1995, seeds were planted and grown.

In 1996, scions were grafted on top of root stock.

In 1998, the first fruit was harvested.

In 2003, lines were primarily selected.

In 2009, plants were secondary selected.

From 2010 to 2022 there were growing tests for their performance.

In 2023, breeding was completed with DUS status confirmed (distinct, uniform, and stable), whereby it was confirmed that the instant tree reproduces true to type in successive generations of asexual reproduction, and the variety was named 'Mikanken10'.

Cultivation of variety does not require special conditions or treatments.

The variety is currently mainly intended for fruit production.

SUMMARY OF THE VARIETY

This new mandarin plant 'Mikanken10' has dense spines on the tree, leaf blade with emargination at tip, fruit with flattened general shape of distal part, that distinguish it notably from its male parent 'ARIAKE', and no navel opening, that distinguish it notably from its female parent 'NANKO'.

Also, 'Mikanken10' has no depression at the distal end of the fruit and no polyembryony of seeds, that distinguishes it notably from comparative variety 'SEINANNOHIKARI' (not patented in the U.S.).

In addition, the fruit of 'Mikanken10' has the following characteristics: The fruit size is approximately 200 g, the predominant color of the fruit surface is vivid orange, the rind thickness is thin, the strength of the segment walls is weak, the fruit has no seeds, in early December, the total soluble solids (Brix) of juice is about 15 degrees and the juice acidity is medium, and the time of maturity of the fruit is in early to mid-December.

Table 1 shows a comparison between the instant variety 'Mikanken10' and Male parent variety 'ARIAKE' and Female parent variety 'NANKO', as follows (average evaluation):

TABLE 1

Comparison between 'Mikanken10' and 'ARIAKE' and 'NANKO'

| No. | Characteristics | Male parent variety 'ARIAKE' States | Female parent variety 'NANKO' States | Present variety 'Mikanken10' States |
|---|---|---|---|---|
| 3 | Tree: density of spine | Absent or Sparse | Intermediate | Dense |
| 15 | Leaf blade: emargination at tip | Absent | Absent | Present |
| 41 | Fruit: general shape of distal part | Slightly rounded | Slightly rounded | Flattened |
| 48 | Fruit: presence of navel opening | Absent | Always present | Absent |

Table 2 shows a comparison between the instant variety 'Mikanken10' and comparative variety 'SEINANNNOHIKARI', as follows (average evaluation):

TABLE 2

Comparison between 'Mikanken10' and 'SEINANNOHIKARI'

| No. | Characteristics | Comparative variety 'SEINANNOHIKARI' States | Present variety 'Mikanken10' States |
|---|---|---|---|
| 15 | Leaf blade: emargination at tip | Absent | Present |
| 42 | Fruit: presence of depression at distal end | Present | Absent |
| 91 | Seed: poly-embryony | Present | Absent |

BRIEF DESCRIPTION OF THE DRAWINGS

In the accompanying drawings, which are as nearly true as is reasonable possible to make in a color illustration of this type.

Figure 1:
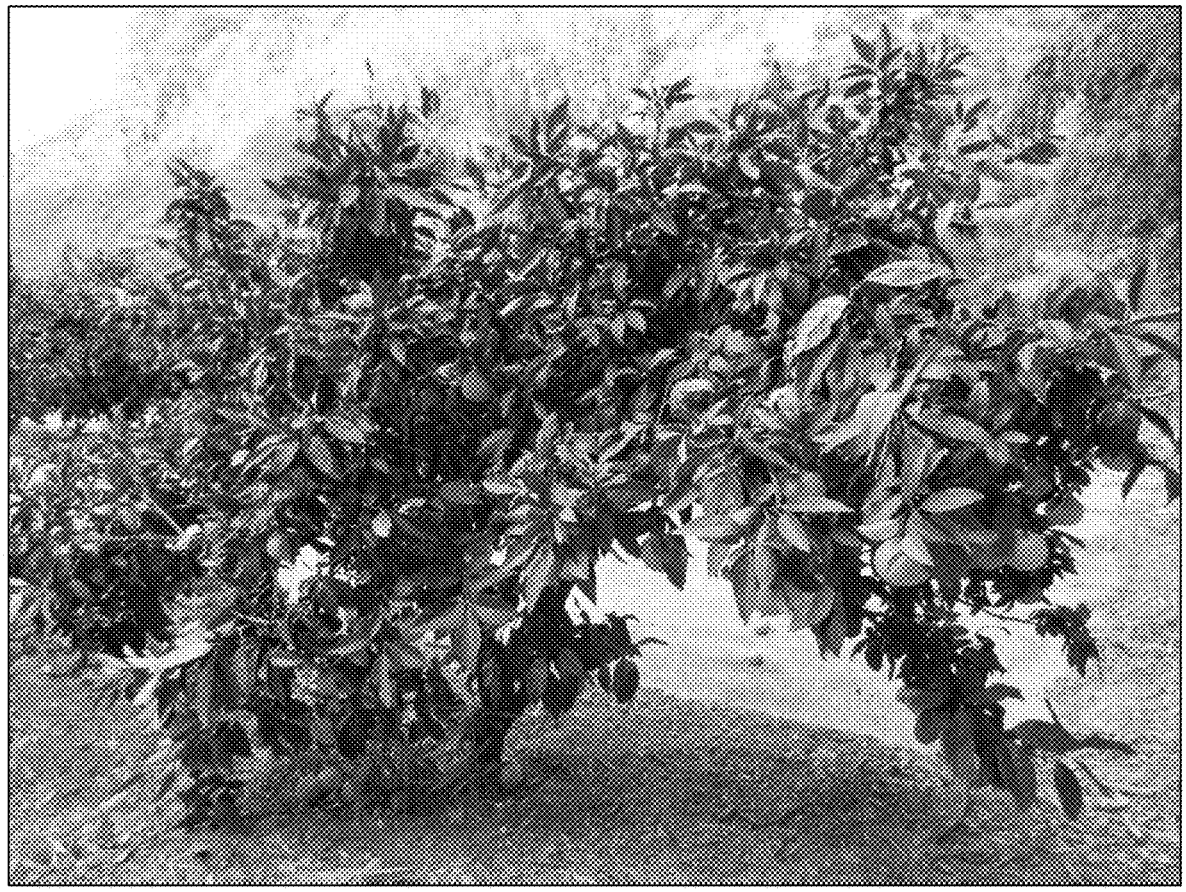
FIG. 1 is a color photograph showing a general view of an illustrative mandarin tree of the variety named 'Mikanken10' bearing fruits.
Figure 2:
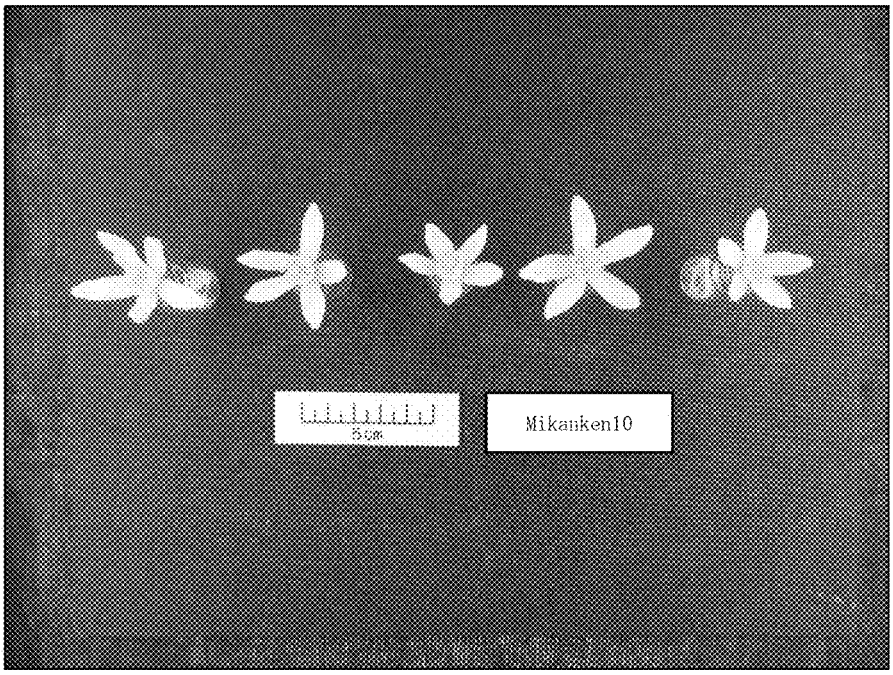
FIG. 2 is a color photograph showing flowers of 'Mikanken10'.
Figure 3:
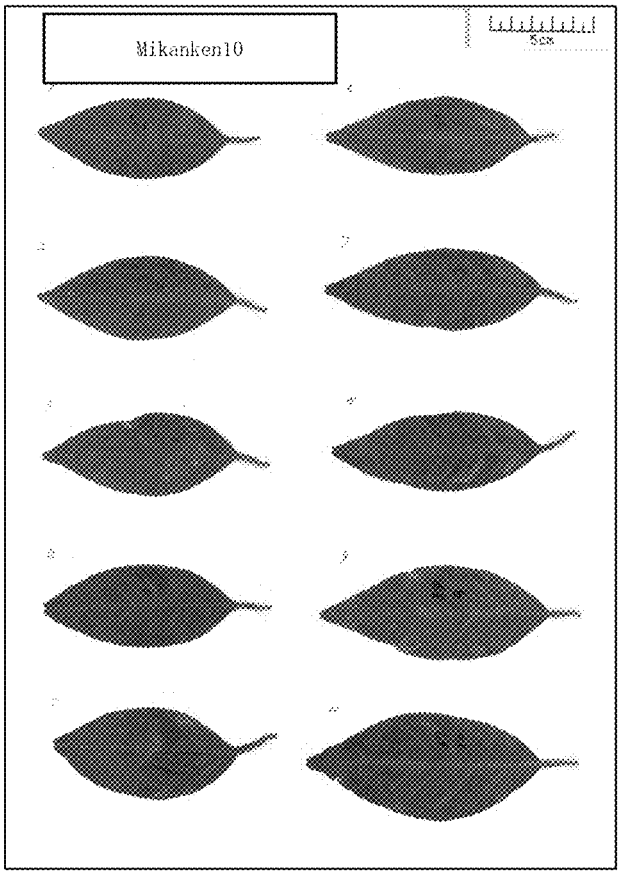
FIG. 3 is a color photograph showing upper surfaces of leaves of 'Mikanken10'.
Figure 4:
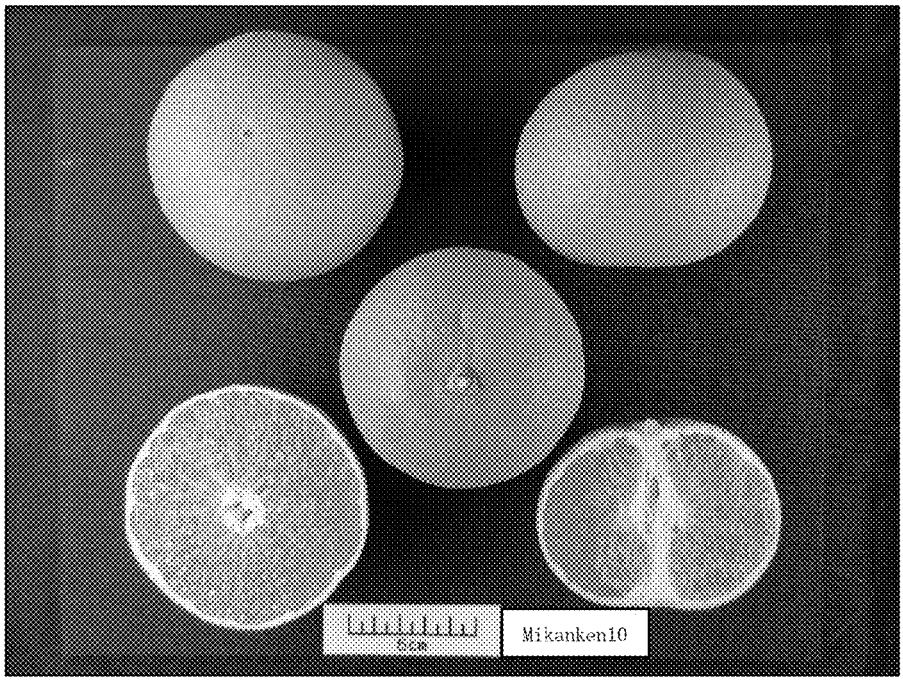
FIG. 4 is a color photograph showing whole fruits (distal end, side view and stalk end), and transverse section and longitudinal section of fruits of 'Mikanken10'.
Figure 5:
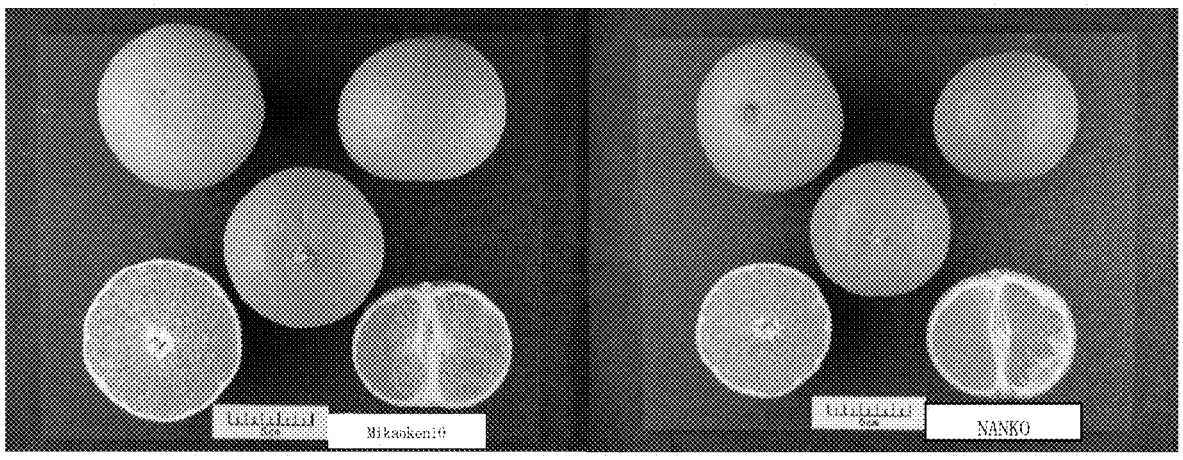
FIG. 5 is a color photograph showing whole fruits (distal end, side view and stalk end), and transverse section and longitudinal section of fruits of 'Mikanken10' and 'NANKO', which is indicating difference of fruit: navel opening.
Figure 6:
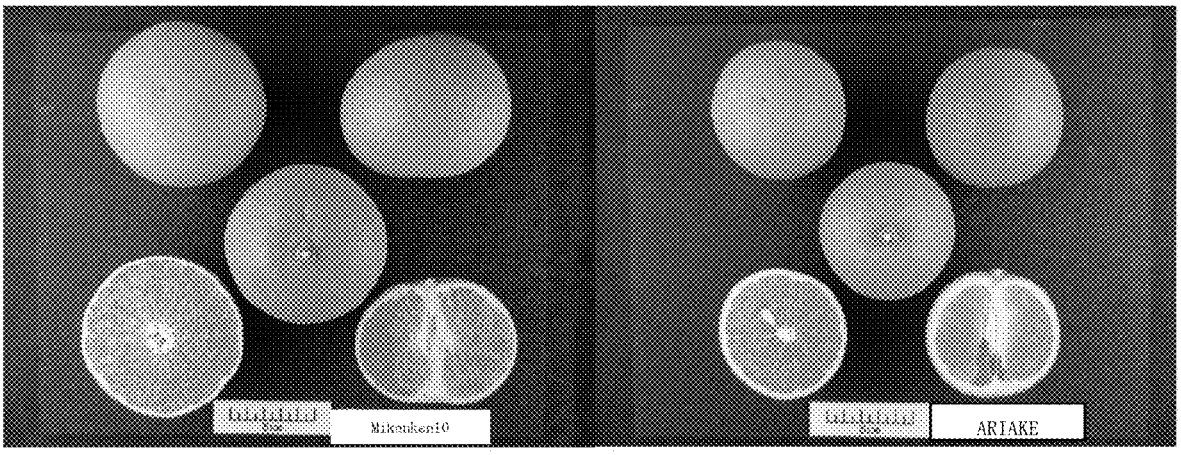
FIG. 6 is a color photograph showing whole fruits (distal end, side view and stalk end), and transverse section and longitudinal section of fruits of 'Mikanken10' and 'ARIAKE', which is indicating difference of general shape of distal part.
Figure 7:
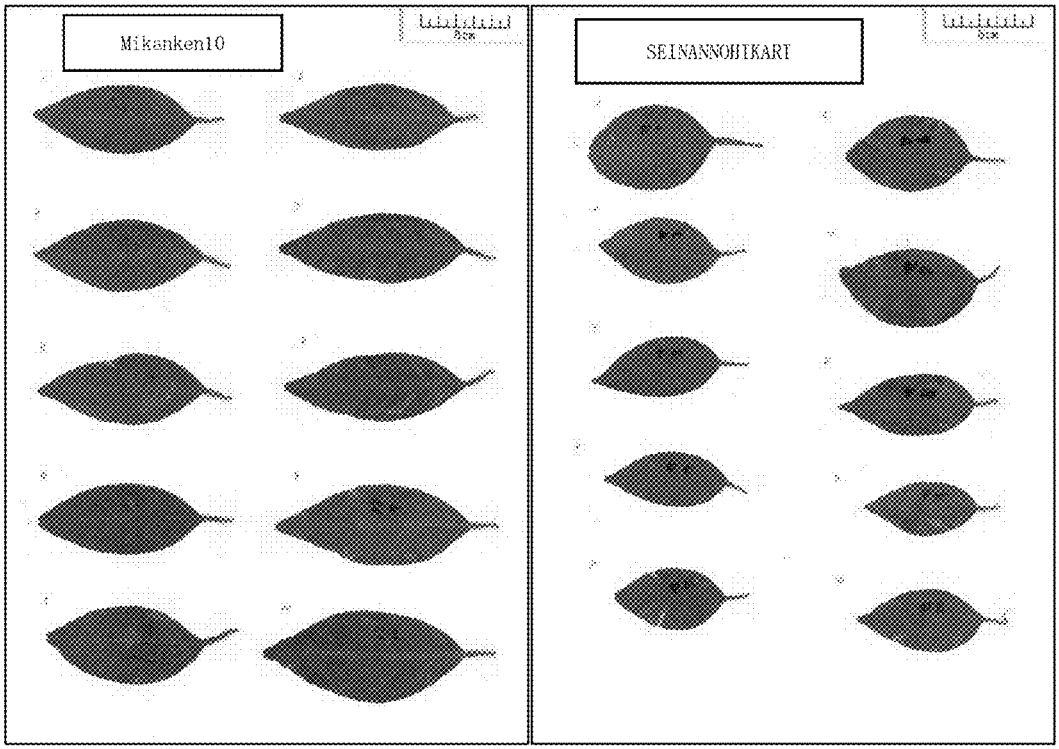
FIG. 7 is a color photograph showing upper surfaces of leaves of 'Mikanken10' and 'SEINANNOHIKARI', which is indicating difference of leaf: emargination at tip.

Due to chemical and/or digital development, processing and printing, the plants or portions of plants depicted in the photographs may or may not be precisely accurate when compared to the actual botanical specimens.

DETAILED DESCRIPTION OF THE INVENTION

Table 3 shows the botanical description of the 'Mikanken10' plants evaluated in 2023. The values as provided are averages. The ages of the trees evaluated was 15 years after grafted on top of rootstock, and the location of the trees evaluated was in Uwajima, Ehime, Japan.

Colors are given according to the J.H.S. (Japan Horticultural Society) Color Chart.

BOTANICAL DESCRIPTION

TABLE 3

Botanical description of 'Mikanken10'

| No. | Characteristics | States | Values |
|---|---|---|---|
| 1. | Ploidy | Diploid | |
| 2. | Tree: growth habit | Spreading | |
| 3. | Tree: average height | | 2.1 m |
| 4. | Tree: average spread | | 3.0 m |
| 5. | Trunk: average diameter at 10 cm above the grafted area | | 6.8 cm |
| 6. | Trunk: surface texture | | rough |
| 7. | Trunk: bark color | Dark yellow-green | 3107 (JHS Color Chart) |
| 8. | Branches: average length | | 11.3 cm |
| 9. | Branches: surface texture | | smooth |
| 10. | Branches: bark color | Dark yellow-green | 3508 (JHS Color Chart) |
| 11. | Tree: density of spines (number of thorns per total number of leaf-bearing nodes, multiplied by 100) | Dense | 33.3% |
| 12. | Length of spines | | 0.4 cm |
| 13. | Spine: color | Dark yellow-green | 3508 (JHS Color Chart) |
| 14. | Leaf blade: length (apical leaflet in | Long | 10.1 cm |

TABLE 3-continued

Botanical description of 'Mikanken10'

| No. | Characteristics | States | Values |
|---|---|---|---|
| | case of compound leaf) | | |
| 15. | Leaf blade: width (apical leaflet in case of compound leaf) | Medium | 4.2 cm |
| 16. | Leaf blade: ratio length/width (apical leaflet in case of compound leaf) | Medium | 2.4 |
| 17. | Leaf blade: shape in cross section (apical leaflet in case of compound leaf) | Inter-mediate | |
| 18. | Leaf blade: twisting | Absent or Weak | |
| 19. | Leaf blade: blistering | Absent or Weak | |
| 20. | Leaf blade: color: upper surface | Dark yellow-green | 3509 (JHS Color Chart) |
| 21. | Leaf blade: un-dulation of margin | Absent or Weak | |
| 22. | Leaf blade: incisions of margin | Absent | |
| 23. | Leaf blade: shape of apex | Acute | |
| 24. | Leaf blade: emargin-ation at tip | Present | |
| 25. | Petiole: length | Medium | 1.6 cm |
| 26. | Petiole: color | Deep yellow-green | 3507 (JHS Color Chart) |
| 27. | Petiole: presence of wings | Present | |
| 28. | Varieties with petiole wings present only: petiole: width of wings | Narrow | 2.9 mm |
| 29. | Petiole wings: color | Dark yellow-green | 3509 (JHS Color Chart) |
| 30. | Flower: diameter of Calyx | | 0.8 cm |
| 31. | Flower: length of petal | Medium | 15.8 mm |
| 32. | Flower: width of petal | Very Broad | 7.0 mm |
| 33. | Flower: ratio length/ width of petal | | 2.3 |
| 34. | Flower: length of stamens | | 9.0 mm |
| 35. | Blooming period | Early May | |
| 36. | Fragrance | Present | |
| 37. | Flower bud: color | Yellowish white | 2502 (JHS Color Chart) |
| 38. | Sepals: number per flower | | 5 |
| 39. | Sepals: length | | 0.25 cm |
| 40. | Sepals: width | | 0.78 cm |
| 41 | Petal: shape | Spindle-shaped | |
| 42. | Petal: color (upper surface) | Yellowish white | 2502 (JHS Color Chart) |
| 43. | Petal: apex shape | Acute | |
| 44. | Petal: base shape | Round | |
| 45. | Anther: color | Bright reddish yellow | 2204 (JHS Color Chart) |
| 46. | Style: length | | 5.0 mm |
| 47. | infructescence: clustering of fruits | Present | |
| 48. | Fruit: length | | 6.2 cm |
| 49. | Fruit: diameter | | 7.4 cm |
| 50. | Fruit: ratio length/ diameter | | 1.19 |

TABLE 3-continued

Botanical description of 'Mikanken10'

| No. | Characteristics | States | Values |
|---|---|---|---|
| 51. | Fruit: position of broadest part | At Middle | |
| 52. | Fruit: shape in trans-verse section | Circular | |
| 53. | Fruit: general shape of proximal part (excluding neck, collar and depression at stalk end) | Flattened | |
| 54. | Fruit: presence of neck | Absent | |
| 55. | Fruit: presence of depression at stalk end | Absent | |
| 56. | Fruit: presence of con-striction at stalk end | Absent | |
| 57. | Fruit: number of radial grooves at stalk end | Absent or few | 2 |
| 58. | Fruit: length of radial grooves at stalk end | | 7.2 mm |
| 59. | Fruit: presence of collar | Absent | |
| 60. | Fruit: abscission layer between floral disc and fruit | Absent weekly developed | |
| 61. | Fruit: general shape of distal part (excluding nipple, bulging of navel and depression at distal end) | Flattened | |
| 62. | Fruit: presence of depression at distal end | Absent | |
| 63. | Fruit: presence of areola | Incomplete | |
| 64. | Fruit: type of areola | Smooth | |
| 65. | Fruit: diameter of areola | | 3.0 cm |
| 66. | Fruit: diameter of stylar scar | | 3.0 mm |
| 67. | Fruit: persistence of style | None | |
| 68. | Fruit: presence of navel opening | Absent | |
| 69. | Fruit: presence of radial grooves at distal end | Absent | |
| 70. | Fruit surface: pre-dominant color(s) | Vivid orange | 1605 (JHS Color Chart) |
| 71. | Fruit surface: glossiness | Medium | |
| 72. | Fruit surface: roughness | Medium | |
| 73. | Fruit surface: size of oil glands | All more or less the same size | |
| 74. | Fruit surface: size of larger oil glands | Medium | |
| 75. | Fruit surface: con-spicuousness of larger oil glands | Medium | |
| 76. | Fruit surface: presence of pitting and pebbling on oil glands | Pitting absent, Pebbling present | |
| 77. | Fruit: varieties with fruit surface: pebbling on oil glands only: surface: density of pebbling | Medium | |
| 78. | Fruit: varieties with fruit surface: pebbling on oil glands only: surface: degree of pebbling | Medium | |
| 79. | Fruit: rind thickness | Thin | 2.5 mm |
| 80. | Fruit: rind adherence of flesh | Weak to medium | |
| 81. | Fruit: rind: strength | Medium | |
| 82. | Fruit: rind: oiliness | Dry | |
| 83. | Fruit: rind conspicuous-ness of oil glands on inner surface | Absent or weakly conspicuous | |
| 84. | Fruit: color of albedo | Pale yellow | 2503 (JHS Color Chart) |

TABLE 3-continued

Botanical description of 'Mikanken10'

| No. | Characteristics | States | Values |
|---|---|---|---|
| 85. | Fruit: density of albedo | Medium | |
| 86. | Fruit: amount of albedo adhering to flesh (strand excluded) | Small | |
| 87. | Fruit: presence of albedo strands | Present | |
| 88. | Fruit: amount of albedo strands | Medium | |
| 89. | Fruit: main color of flesh | Strong orange | 1606 (JHS Color Chart) |
| 90. | Fruit: filling of core | Medium | |
| 91. | Fruit: diameter of core | Very small | 8.2 mm |
| 92. | Fruit: presence of rudimentary segments | Absent or very weak | |
| 93. | Fruit: number of well-developed segments | | 13 |
| 94. | Fruit: coherence of adjacent segment walls | Medium | |
| 95. | Fruit: strength of segment walls | Weak | |
| 96. | Fruit: length of juice vesicles | | 6.5 mm |
| 97. | Fruit: thickness of juice vesicles | | 2.6 mm |
| 98. | Fruit; conspicuousness of juice vesicle walls | High | |
| 99. | Fruit; coherence of juice vesicles | Medium | |
| 100. | Fruit: presence of navel (viewed internally) | Absent or very rare | |
| 101. | Fruit: juiciness | High | |
| 102. | Fruit: juice: total soluble solids | High | 14.9 (Brix) |
| 103. | Fruit: juice: acidity | Medium | 1.00 |

TABLE 3-continued

Botanical description of 'Mikanken10'

| No. | Characteristics | States | Values |
|---|---|---|---|
| 104. | Fruit: strength of fiber | Weak | |
| 105. | Fruit: number of seeds (open pollinated) | Absent or very few | 0.7 |
| 106. | Seed: polyembryony | Absent | |
| 107. | Seed: length | | 9.6 mm |
| 108. | Seed: width | | 7.2 mm |
| 109. | Seed: surface | Wrinkled | |
| 110. | Seed: varieties with seed surface: wrinkled only: seed: prominence of wrinkled | Medium | |
| 111. | Seed: external color | Whitish | |
| 112. | Seed: color of inner seed coat | Light brown | |
| 113. | Plant: time of maturity of fruit for consumption | Very early to early | December |
| 114. | Plant: fruit: parthenocarpy | Present | |
| 115. | Plant: fruit harvest period | November | |

Other features of the plant are as follows:

Disease and pest resistance: Not observed to date.

Tree hardiness: USDA Hardiness Zone 9a-9b (until −3° C.).

Shipping quality, storage life, and productivity (weight/plant): Under investigation to date. Market use is as a *Citrus* fruit for eating raw.

The invention claimed is:

1. A new and distinct variety of *Citrus* sp. plant named 'Mikanken10', substantially as described and illustrated herein.

* * * * *